United States Patent [19]

Vora et al.

[11] 4,280,880
[45] Jul. 28, 1981

[54] METHOD OF OPERATING AN ISOSTRIPPER COLUMN

[75] Inventors: Bipin V. Vora, Elk Grove Village; Anthony G. Vickers, Arlington Heights, both of Ill.

[73] Assignee: UOP Inc., Des Plaines, Ill.

[21] Appl. No.: 181,032

[22] Filed: Aug. 25, 1980

[51] Int. Cl.³ .......................... B01D 3/06; C07C 2/56
[52] U.S. Cl. ....................................... 203/23; 203/27; 203/88; 203/94; 203/DIG. 19; 585/719; 585/723; 585/800
[58] Field of Search ................... 203/26, 27, DIG. 19, 203/99, 88, 75, 77, 100, DIG. 8, 23, 94, 98; 62/26, 31; 585/723, 719, 709, 800, 802, 911; 208/351

[56] References Cited

U.S. PATENT DOCUMENTS

| | | | |
|---|---|---|---|
| 3,370,003 | 2/1968 | Borst | 585/719 |
| 3,402,124 | 9/1968 | Jones | 203/27 |
| 3,494,861 | 2/1970 | Munro | 203/27 |
| 3,568,457 | 3/1971 | Briggs et al. | 203/26 |
| 4,115,471 | 9/1978 | Kesler | 203/88 |
| 4,137,129 | 1/1979 | Bjorklund | 203/88 |
| 4,180,526 | 12/1979 | Chapman | 585/719 |

*Primary Examiner*—Wilbur L. Bascomb, Jr.
*Attorney, Agent, or Firm*—James R. Hoatson, Jr.; Robert W. Welch; William H. Page, II

[57] ABSTRACT

A process for the separation of isobutane from an alkylation reaction zone hydrocarbon effluent stream comprising isobutane, n-butane, propane and alkylate is disclosed. The hydrocarbon effluent stream is charged to an isostripper column. An isobutane vapor stream from the column is condensed in indirect heat exchange with the lower liquid stream from said column comprising n-butane. The lower liquid stream is flashed in indirect heat exchange with said vapor stream at conditions to provide a vapor phase, said vapor phase being compressed and recycled to said column at a temperature to promote vapor formation therein.

8 Claims, 1 Drawing Figure

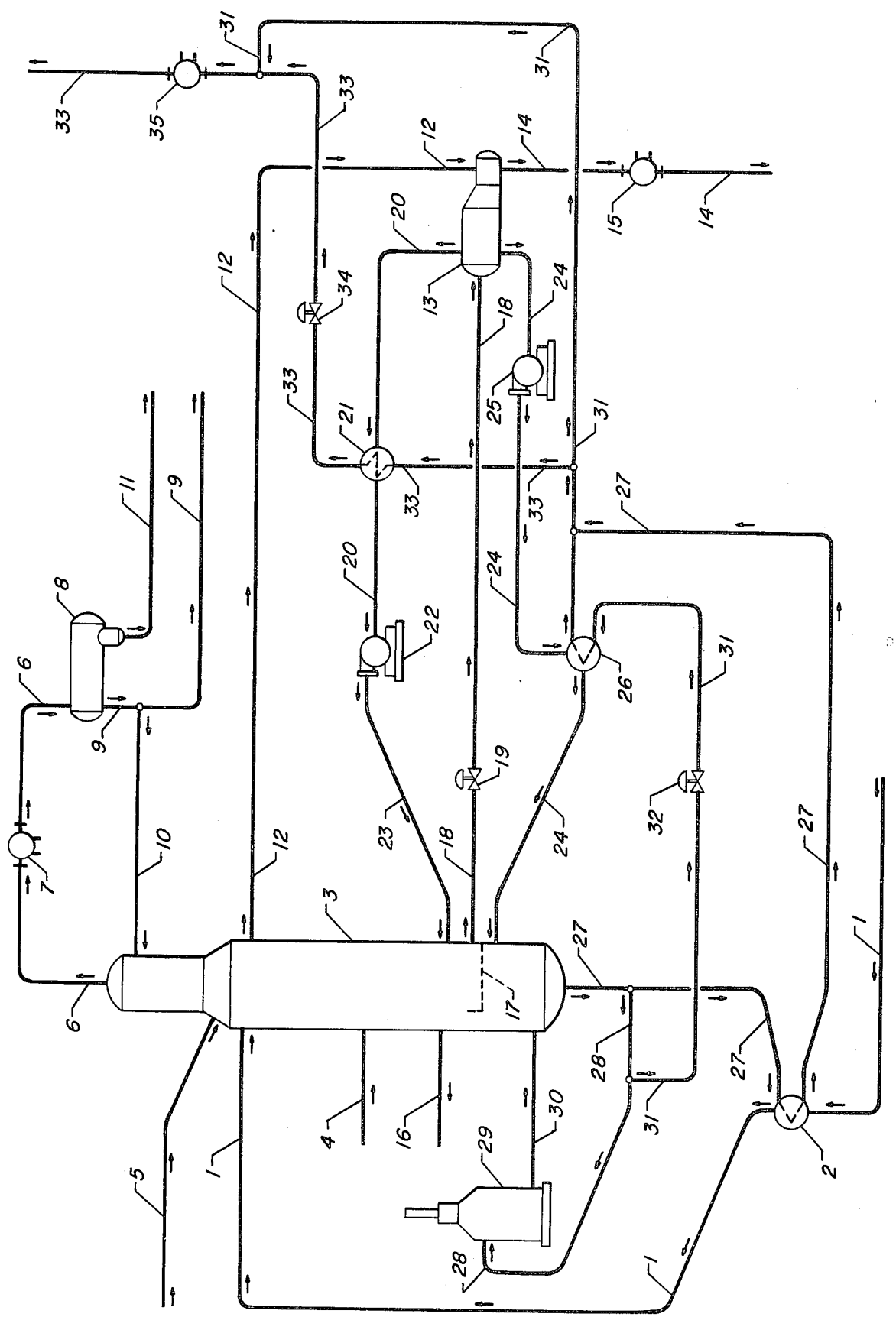

METHOD OF OPERATING AN ISOSTRIPPER COLUMN

This invention relates to a process for the acid-catalyzed alkylation of an isoparaffin with an olefin, or an olefin-acting compound, as the alkylating agent. The acid-catalyzed alkylation process herein contemplated is almost invariably a hydrofluoric acid-catalyzed process. The alkylation of normally gaseous isoparaffinic hydrocarbons, typically isobutane, with normally gaseous $C_3$–$C_5$ olefinic hydrocarbons to yield normally liquid, higher molecular weight isoparaffinic hydrocarbons, has long been recognized in the petroleum industry as a valuable tool in the manufacture of gasoline products high in octane value. The $C_3$–$C_5$ olefinic hydrocarbon is most often propylene, butylenes or a mixture of propylene and butylenes. Since its inception, the process has experienced many changes and improvements with respect to unit design and operating technique.

In the alkylation process, it has been the practice to maintain a substantial molar excess of the isoparaffin reactant in the alkylation reaction zone. This reduces the tendency of the olefinic component of the reaction mixture to undergo polymerization in preference to alkylation. A hydrocarbon effluent from an alkylation reaction zone wherein isobutane is alkylated with a propylene-butylene mixture will thus comprise the excess isobutane as well as propane and n-butane, as is typically the case, and the alkylate product. The separation and recovery of said propane for use, for example, as a fuel, and the separation and recovery of n-butane for use, for example, as a gasoline blending agent, and, more importantly, the separation and recovery of isobutane for recycle to the alkylation reaction zone, is largely the function of a fractionation column commonly referred to as an isostripper column.

The hydrocarbon portion of the effluent stream from the alkylation reaction zone is introduced into the upper section of the isostripper column. A controlled amount of heat is applied to the bottom of the column, and a controlled amount of cooling is applied to the top. The operation of the isostripper further entails the use of a reboiler such as is commonly employed to promote vapor formation in the lower column. Fractionation conditions of temperature and pressure are selected to allow the separation of propane as an overhead fraction, isobutane as an upper intermediate fraction withdrawn below the hydrocarbon feed point, and n-butane as a lower intermediate fraction, the alkylate being withdrawn from the bottom of the isostripper column. The various propane, isobutane, n-butane and alkylate streams are generally cooled by heat exchange methods to promote reflux, facilitate recycle to the exothermic alkylation reaction, or for ease of storage, as the case may be. It will be appreciated that the heating and cooling process as applied to the various streams necessarily results in a substantial heat loss to the system.

It is an object of this invention to utilize the heat from a vapor stream withdrawn from a fractionation or isostripper column to impart heat to a lower portion of said column and promote vapor formation therein. It is another object to provide a method for condensing a vapor stream from a fractionation or isostripper column whereby said vapor stream is condensed in indirect heat exchange with a lower liquid stream withdrawn from said column, said lower liquid stream being flashed in indirect heat exchange with said vapor stream at conditions to provide a vapor phase, said vapor phase being compressed and recycled to said column at a temperature to promote vapor formation therein.

In one of its broad aspects, the present invention embodies a process for the separation of isobutane from an alkylation reaction zone hydrocarbon effluent stream comprising said isobutane, n-butane, propane and alkylate, which comprises the steps of (a) passing said effluent stream into a fractionation column operated at fractionation conditions; (b) separating said propane as an overhead vapor stream; (c) withdrawing an isobutane vapor stream from said column as an upper intermediate fraction, at least partially condensing said vapor stream by indirect heat exchange with a lower intermediate fraction withdrawn from said column pursuant to step (d), and recovering said isobutane stream; (d) withdrawing a liquid stream comprising n-butane from said column as said lower intermediate fraction, effecting a reduction in pressure and temperature of said stream, and flashing said stream by indirect heat exchange with said upper intermediate fraction pursuant to step (c); (e) separating and compressing the resulting vapor phase to form a recycle stream having a temperature and pressure substantially equivalent to the lower intermediate fraction as withdrawn from said column, and introducing said recycle stream into the lower portion of said column at a point above the level of withdrawl of said lower intermediate fraction; and, (f) recovering the liquid phase of said mixed phase stream, heating said liquid phase by indirect heat exchange with the alkylate product stream withdrawn as the bottoms fraction from said column, and recycling said liquid phase from said column to the lower portion of said column at a point below the level of withdrawal of said lower intermediate fraction.

One of the most specific embodiments of this invention concerns a process for the separation of isobutane from an alkylation reaction zone hydrocarbon effluent stream which comprises the steps of (a) passing said effluent stream into a fractionation column operated at a bottom temperature of from about 350° to about 390° F., a top temperature of from about 125° to about 150° F., a bottom pressure of from about 155 to about 165 psig. and a top pressure of from about 145 to about 155 psig.; (b) separating propane as an overhead vapor stream; (c) withdrawing an isobutane vapor stream from said column at a temperature of from about 160° to about 180° F. as an upper intermediate fraction, at least partially condensing said vapor stream by indirect heat exchange with a lower intermediate fraction withdrawn from said column pursuant to step (d), and recovering said isobutane stream; (d) withdrawing a liquid stream comprising n-butane from said column at a temperature of from about 190° to about 205° F. and at a pressure of from about 155 to about 165 psig. as said lower intermediate fraction, effecting a reduction in pressure to from about 70 to about 80 psig. and flashing said liquid stream at a temperature of from about 140° to about 150° F. by indirect heat exchange with said upper intermediate fraction pursuant to step (c) and effecting the vaporization of from about 85 to about 95% thereof; (e) separating and preheating the resulting vapor phase by indirect heat exchange with the alkylate product stream, and compressing said vapor phase to form a recycle stream having a temperature and pressure substantially equivalent to the lower intermediate fraction as withdrawn from said column, and introducing said recycle stream into the lower portion of said column at a point above the level of withdrawal of said lower intermediate fraction; and, (f) recovering the liquid phase of said mixed phase stream, heating said liquid phase by indirect heat exchange with the alkylate product stream withdrawn as the bottoms fraction from said column, and recycling said liquid phase from said column to the lower portion of said column at a point below the level of withdrawal of said lower intermediate fraction.

Other objects and embodiments of this invention will become apparent in the following detailed specification.

The further description of the process of this invention is presented with reference to the attached schematic drawing. The drawing represents one preferred embodiment of the invention and is not intended as an undue limitation on the generally broad scope of the invention as set out in the appended claims. Only those compressors, heaters, heat-exchangers, coolers and valves are shown that are useful in the description of the process. The utilization of other miscellaneous hardware such as pumps, instrumentation and controls have been omitted as not essential to a clear understanding of the process, the use of such hardware being well within the purview of one skilled in the art.

Referring then to the drawing, there is shown an isostripper column 3. The isostripper column is typically operated at fractionation conditions including a bottom temperature of from about 350° to about 390° F., a top temperature of from about 125° to about 150° F., a bottom pressure of from about 155 to about 165 psig., and a top pressure of from about 145 to about 155 psig. In the present example, an alkylation reaction zone effluent stream, at a temperature of about 100° F., is charged to a heat exchanger 2 contained in line 1 whereby said stream is heated to a temperature of about 150° F. by indirect heat exchange with the hot alkylate product stream recovered from the isostripper column by way of line 27. The alkylation reaction zone effluent stream is continued through line 1 to provide about 271.4 moles of propane, 2721.4 moles of isobutane, 649.9 moles of n-butane, 29.4 moles of isopentane, 1.3 moles of n-pentane and about 394.6 moles of $C_{6}+$ hydrocarbons per hour to the isostripper column 3. Said alkylation reaction zone effluent stream further contains about 125.7 moles of HF per hour, the mole quantities expressed herein being intended as lb-moles.

Also charged to the isostripper column 3 is a field butanes stream comprising about 33.5 moles of propane, 307.7 moles of isobutane, 809.6 moles of n-butane, 8.4 moles of isopentane and 2.8 moles of n-pentane per hour. The field butanes stream is introduced into the isostripper column by way of line 4 at a temperature of about 173° F. Also introduced into the isostripper column is an overhead stream from an HF acid regenerator, as shown, said overhead stream entering said column at a temperature of approximately 160° F. via line 5 to further provide about 3.7 moles of propane, 98.9 moles of isobutane, 13.3 moles of n-butane, 0.1 mole of isopentane, 0.05 mole of n-pentane, 0.2 mole of $C_{6}+$ hydrocarbons and 71.7 moles of HF per hour.

An overhead vapor stream is recovered by way of line 6 from the isostripper column 3 at a temperature of about 140° F., and this vapor stream is directed through a condenser 7 to an overhead receiver 8. The resulting condensed vapor stream is recovered through line 9 and comprises, on an hourly basis, about 257.1 moles of propane, 497.8 moles of isobutane, 51.7 moles of n-butane and 21.4 moles of HF acid. A portion of this stream is diverted from line 9 through line 10 to serve as a reflux agent in the isostripper column, and the balance of said stream is continued through line 9 to a depropanizer column which is not shown. The HF acid which settles out in the overhead receiver 8 is recovered through line 11 at a rate of approximately 160.8 moles per hour.

An upper intermediate fraction, a vapor stream, is withdrawn from the isostripper column through line 12. This vapor stream comprises, on an hourly basis, about 223.1 moles of propane, 2943.7 moles of isobutane, 618.4 moles of n-butane, 14.2 moles of isopentane, 0.5 mole of n-pentane, 19.3 moles of $C_{6}+$ hydrocarbons and 29.4 moles of HF acid. The vapor stream is passed to an upper reboiler 13 at a temperature of from about 160° to about 170° F. and at a pressure of approximately 143 psig. to effect an indirect heat exchange therein as hereinafter related. The isobutane-rich stream is recovered from said reboiler through line 14 and a condenser 15 for recycle to the alkylation reaction zone as is the common practice.

An intermediate fraction, comprising principally n-butane, is separated as a sidecut through line 16. This n-butane-rich vapor stream is condensed and recovered for use, for example, as a gasoline blending agent. In addition to about 786.5 moles of n-butane, this intermediate fraction further comprises about 21.3 moles of isobutane, 9.3 moles of isopentane, 1.2 moles of n-pentane and 8.1 moles of $C_{6}+$ hydrocarbons, all on an hourly basis.

Pursuant to the present invention, a liquid fraction comprising n-butane is withdrawn from the isostripper column through line 18 as a lower intermediate sidecut, in this instance at about the sixth tray 17 of a 70-tray column, and below the n-butane vapor sidecut withdrawn through line 16. The lower intermediate sidecut withdrawn through line 18 comprises about 5015 moles per hour of mostly n-butane but also lesser amounts of isobutane and $C_{6}+$ hydrocarbons, and said sidecut is withdrawn from the isostripper column at a pressure of from about 155 to about 165 psig. and at a temperature of from about 195° to about 205° F. This liquid stream is passed through a pressure reducing valve 19 and enters the aforementioned upper reboiler 13 at a pressure of from about 70 to about 80 psig. and reduced in temperature to approximately 140°–150° F. In the upper reboiler 13, from about 85% to about 95% of the liquid stream is vaporized by indirect heat exchange with the previously described hot isobutane vapor stream introduced to the upper reboiler from line 12. The vaporized material is recovered from said reboiler through an overhead line 20 and a heat exchanger 21 whereby it is increased in temperature to about 155° F. by indirect heat exchange with a hot alkylate product stream passing through line 33 at a temperature of about 219° F. The vapor stream is continued through line 20 to a compressor 22 whereby it is increased in pressure to about 160 psig. and in temperature to about 200° F. The vapor stream is then returned to the isostripper column as upper reboiler vapors through line 23.

The liquid phase from the upper reboiler 13, i.e. that portion of the liquid fraction withdrawn from the isostripper column through line 18 and not vaporized in said reboiler, is recovered through line 24 and a compressor 25 and recycled to the lower portion of the isostripper column as upper reboiler liquid return at a point below the aforementioned tray 17. The liquid stream is recycled through a heat exchanger 26 whereby, by indirect heat exchange with a portion of the hot alkylate product stream passing through line 31, said liquid stream is raised in temperature to at least about 200° F. and returned to the isostripper column at a pressure of about 160 psig.

A hot alkylate product stream is recovered from the bottom of the isostripper column by way of line 27, one portion of said product stream being diverted from line 27 and recycled through line 28, a lower reboiler 29 and line 30 to the isostripper column to maintain a bottom temperature therein of from about 350° to about 390° F. A second portion of the alkylate product stream is diverted from line 27 by way of line 28 and line 31. This alkylate product stream is passed through a temperature control valve 32 which is responsive to the temperature of the liquid stream in line 24, and said product stream is continued through line 31 to the previously mentioned heat exchanger 26 at a temperature of about 386° F. whereby the previously mentioned liquid stream recycled through line 24 is elevated in temperature to about 200° F. by indirect heat exchange as heretofore described.

The balance of the alkylate product stream recovered from the isostripper column through line 27 is continued through line 27 at a temperature of about 345° F. to the described heat exchanger 2 whereby the alkylation reaction zone effluent passing through line 1 is heated to a temperature of about 150° F. by indirect heat exchange. The alkylate product stream is then continued through line 27 and combined in line 31 with the effluent alkylate product stream from the heat exchanger 26. One portion of the combined streams is diverted from line 31 by way of line 33 and charged to the aforementioned heat exchanger 21 at a temperature of about 219° F. whereby the vapor stream passing through line 20 is heated by indirect heat exchange to a temperature of about 155° F. as aforesaid. The alkylate product stream from the heat exchanger 21 is recovered through a temperature control valve 34 which is responsive to the temperature of the upper reboiler vapors passing through line 23. The alkylate product stream is then discharged through a cooler 35 in combination with the remaining portion of the alkylate product stream from line 31 at a temperature of about 100° F. The alkylate product stream discharged through line 33 comprises about 375.5 moles of $C_6+$ hydrocarbons, 0.4 mole of isobutane, 28.5 moles of n-butane, 18.5 moles of isopentane and 2.8 moles of n-pentane per hour.

In the separation of the alkylation reaction zone hydrocarbon effluent in the isostripper column, a heat exchanger is typically required to condense the isobutane vapors recovered as the upper intermediate fraction that they may be more readily further processed. Said vapors are condensed in accordance with the present invention by indirect heat exchange with the lower intermediate fraction in the upper reboiler. The need of a heat exchanger has therefore been eliminated. Further, by utilizing the upper intermediate vapor fraction as a source of heat to the upper reboiler, flashing and vaporizing the lower intermediate liquid fraction in said reboiler by indirect heat exchange with the condensing vapors from said vapor fraction, and by compressing the resulting upper reboiler vapors for recycle to the isostripper column at a temperature and pressure substantially commensurate with a lower intermediate liquid fraction withdrawn therefrom, a substantial reduction in the utility requirements of the upper reboiler is effected.

We claim as our invention:

1. A process for the separation of isobutane from an alkylation reaction zone hydrocarbon effluent stream comprising said isobutane, n-butane, propane and alkylate, which comprises the steps of:
   (a) passing said effluent stream into a fractionation column operated at fractionation conditions;
   (b) separating said propane as an overhead vapor stream;
   (c) withdrawing an isobutane vapor stream from said column as an upper intermediate fraction, at least partially condensing said vapor stream by indirect heat exchange with a lower intermediate fraction withdrawn from said column pursuant to step (d), and recovering said isobutane stream;
   (d) withdrawing a liquid stream comprising n-butane from said column as said lower intermediate fraction, effecting a reduction in pressure and temperature of said stream, and flashing said stream by indirect heat exchange with said upper intermediate fraction pursuant to step (c);
   (e) separating and compressing the resulting vapor phase to form a recycle stream having a temperature and pressure substantially equivalent to the lower intermediate fraction as withdrawn from said column, and introducing said recycle stream into a lower portion of said column at a point above the level of withdrawl of said lower intermediate fraction;
   (f) recovering the liquid phase of said mixed phase stream, heating said liquid phase by indirect heat exchange with the alkylate product stream withdrawn as the bottoms fraction with said column, and recycling said liquid phase from said column to the lower portion of said column at a point below the level of withdrawl of said lower intermediate fraction.

2. The process of claim 1 further characterized with respect to step (a) in that said fractionation conditions include a bottom temperature of from about 350° to about 390° F., a top temperature of from about 125° to about 150° F., a bottom pressure of from about 155 to about 165 psig. and a top pressure of from about 145 to about 155 psig.

3. The process of claim 1 further characterized with respect to step (c) in that said isobutane vapor stream is withdrawn from said column at a temperature of from about 160° to about 180° F.

4. The process of claim 1 further characterized with respect to step (d) in that said liquid stream is withdrawn at a temperature of from about 195° to about 205° F. and at a pressure of from about 155 to about 165 psig.

5. The process of claim 1 further characterized with respect to step (d) in that said liquid stream is flashed by indirect heat exchange with said upper intermediate fraction pursuant to step (c) at conditions effecting the vaporization of from about 85 to about 95% thereof.

6. The process of claim 1 further characterized with respect to step (d) in that said liquid stream is reduced in pressure to from about 70 to about 80 psig. and flashed at a temperature of from about 140° to about 150° F. by indirect heat exchange with said upper intermediate fraction pursuant to step (c).

7. The process of claim 1 further characterized with respect to step (f) in that said liquid phase is heated to a temperature of at least about 200° F. by indirect heat exchange with said alkylate product stream.

8. The process of claim 1 further characterized with respect to step (e) in that said resulting vapor phase is separated, preheated by indirect heat exchange with the alkylate product stream, and compressed to form a recycle stream having a temperature and pressure substantially equivalent to the lower intermediate fraction as withdrawn from said column.

* * * * *